US011793780B2

(12) United States Patent
Batra et al.

(10) Patent No.: US 11,793,780 B2
(45) Date of Patent: Oct. 24, 2023

(54) PRODRUGS OF TREPROSTINIL

(71) Applicants: United Therapeutics Corporation, Silver Spring, MD (US); MannKind Corporation, Westlake Village, CA (US)

(72) Inventors: Hitesh Batra, Herndon, VA (US); Liang Guo, Vienna, VA (US); Patrick Poisson, Chapel Hill, NC (US); Sri Harsha Tummala, Owings Mills, MD (US); Elizabeth Ann Harris, Lagrangeville, NY (US)

(73) Assignees: United Therapeutics Corporation, Silver Spring, MD (US); Mann Kind Corporation, Westlake Village, CA (US)

( * ) Notice: Subject to any disclaimer, the term of this patent is extended or adjusted under 35 U.S.C. 154(b) by 318 days.

(21) Appl. No.: 17/342,377

(22) Filed: Jun. 8, 2021

(65) Prior Publication Data
US 2021/0378996 A1 Dec. 9, 2021

Related U.S. Application Data

(60) Provisional application No. 63/036,561, filed on Jun. 9, 2020.

(51) Int. Cl.
*A61K 31/192* (2006.01)
*A61K 47/54* (2017.01)

(52) U.S. Cl.
CPC .......... *A61K 31/192* (2013.01); *A61K 47/545* (2017.08)

(58) Field of Classification Search
CPC ............................ A61K 31/192; A61K 47/545
See application file for complete search history.

(56) References Cited

U.S. PATENT DOCUMENTS

| | | |
|---|---|---|
| 4,306,075 A | 12/1981 | Aristoff |
| 5,153,222 A | 10/1992 | Tadepalli et al. |
| 5,234,953 A | 8/1993 | Crow et al. |
| 6,054,486 A | 4/2000 | Crow et al. |
| 6,441,245 B1 | 8/2002 | Moriarty et al. |
| 6,521,212 B1 | 2/2003 | Cloutier et al. |
| 6,528,688 B2 | 3/2003 | Moriarty et al. |
| 6,700,025 B2 | 3/2004 | Moriarty et al. |
| 6,756,033 B2 | 6/2004 | Cloutier et al. |
| 6,756,117 B1 | 6/2004 | Barnes |
| 6,803,386 B2 | 10/2004 | Shorr et al. |
| 6,809,223 B2 | 10/2004 | Moriarty et al. |
| 7,199,157 B2 | 4/2007 | Wade et al. |
| 7,384,978 B2 | 6/2008 | Phares et al. |
| 7,417,070 B2 | 8/2008 | Phares et al. |
| 7,879,909 B2 | 2/2011 | Wade et al. |
| 7,999,007 B2 | 8/2011 | Jeffs et al. |
| 8,232,316 B2 | 7/2012 | Phares et al. |
| 8,242,305 B2 | 8/2012 | Batra et al. |
| 8,252,839 B2 | 8/2012 | Phares et al. |
| 8,349,892 B2 | 1/2013 | Phares |
| 8,350,079 B2 | 1/2013 | Walsh |
| 8,410,169 B2 | 4/2013 | Phares et al. |
| 8,461,393 B2 | 6/2013 | Sharma |
| 8,481,782 B2 | 7/2013 | Batra et al. |
| 8,497,393 B2 | 7/2013 | Batra et al. |
| 8,536,363 B2 | 9/2013 | Phares et al. |
| 8,563,614 B2 | 10/2013 | Wade et al. |
| 8,609,728 B2 | 12/2013 | Rothblatt et al. |
| 8,653,137 B2 | 2/2014 | Jeffs et al. |
| 8,658,694 B2 | 2/2014 | Jeffs et al. |
| 8,747,897 B2 | 6/2014 | Kidane et al. |
| 8,765,813 B2 | 7/2014 | Wade et al. |
| 8,940,930 B2 | 1/2015 | Batra et al. |
| 9,029,607 B2 | 5/2015 | Mcgowan et al. |
| 9,050,311 B2 | 6/2015 | Phares et al. |
| 9,156,786 B2 | 10/2015 | Batra et al. |
| 9,199,908 B2 | 12/2015 | Phares et al. |
| 9,255,064 B2 | 2/2016 | Malinin et al. |
| 9,278,901 B2 | 3/2016 | Phares et al. |
| 9,278,902 B2 | 3/2016 | Tang et al. |
| 9,278,903 B2 | 3/2016 | Tang et al. |
| 9,339,507 B2 | 5/2016 | Olschewski et al. |
| 9,346,738 B2 | 5/2016 | Jain et al. |
| 9,358,240 B2 | 6/2016 | Olschewski et al. |
| 9,388,154 B2 | 7/2016 | Yiannikouros et al. |
| 9,422,223 B2 | 8/2016 | Phares et al. |
| 9,624,156 B2 | 4/2017 | Phares et al. |
| 9,758,465 B2 | 9/2017 | Laing |
| 9,878,972 B2 | 1/2018 | Phares et al. |
| 2008/0200449 A1 | 8/2008 | Olschewski et al. |
| 2008/0280986 A1 | 11/2008 | Wade et al. |
| 2009/0036465 A1 | 2/2009 | Roscigno et al. |

(Continued)

FOREIGN PATENT DOCUMENTS

| | | |
|---|---|---|
| WO | WO-00/57701 A1 | 10/2000 |
| WO | WO-2013/024052 A1 | 2/2013 |

(Continued)

OTHER PUBLICATIONS

Moriarty et al., JOC Article, "The Intramolecular Asymmetric Pauson-Khand Cyclization as a Novel and General Stereoselective Route to Benzindene Prostacyclins: Synthesis of UT-15 (Treprostinil)," J. Org. Chem., 2004, 69:1890-1902.

(Continued)

*Primary Examiner* — Sikarl A Witherspoon
(74) *Attorney, Agent, or Firm* — Foley & Lardner LLP

(57) ABSTRACT

Provided are novel treprostinil based compounds, methods of treatment using the same, and their methods of making.

20 Claims, No Drawings

(56) References Cited

U.S. PATENT DOCUMENTS

| | | |
|---|---|---|
| 2009/0124697 A1 | 5/2009 | Cloutier et al. |
| 2012/0197041 A1 | 8/2012 | Batra et al. |
| 2013/0184295 A1 | 7/2013 | Sprague et al. |
| 2013/0331593 A1 | 12/2013 | Mcgowan et al. |
| 2014/0024856 A1 | 1/2014 | Giust et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0148414 A1 | 5/2015 | Malinin et al. |
| 2015/0299091 A1 | 10/2015 | Batra et al. |
| 2015/0315114 A1 | 11/2015 | Hering et al. |
| 2015/0328232 A1 | 11/2015 | Malinin et al. |
| 2015/0376106 A1 | 12/2015 | Batra et al. |
| 2016/0030355 A1 | 2/2016 | Kidane et al. |
| 2016/0030371 A1 | 2/2016 | Phares et al. |
| 2016/0045470 A1 | 2/2016 | Reddy et al. |
| 2016/0051505 A1 | 2/2016 | Phares et al. |
| 2016/0107973 A1 | 4/2016 | Batra et al. |
| 2016/0129087 A1 | 5/2016 | Christe et al. |
| 2016/0143868 A1 | 5/2016 | Olschewski et al. |
| 2016/0152548 A1 | 6/2016 | Gao et al. |
| 2016/0175319 A1 | 6/2016 | Freissmuth et al. |
| 2017/0095432 A1 | 4/2017 | Phares et al. |
| 2018/0153847 A1 | 6/2018 | Phares et al. |

FOREIGN PATENT DOCUMENTS

| | | |
|---|---|---|
| WO | WO-2014/160638 A1 | 10/2014 |
| WO | WO-2016/038532 A1 | 3/2016 |
| WO | WO-2016/055819 A1 | 4/2016 |
| WO | WO-2016/081658 A1 | 5/2016 |
| WO | WO-2016/105538 A1 | 6/2016 |
| WO | WO-2018/058124 A1 | 3/2018 |
| WO | WO-2019/115702 A1 | 6/2019 |
| WO | WO-2019/237028 A1 | 12/2019 |

OTHER PUBLICATIONS

Sorbera et al., "UT-15. Treatment of Pulmonary Hypertension Treatment of Peripheral Vascular Disease," Drug of the Future, 2001, 26(4):364-374.

PRODRUGS OF TREPROSTINIL

RELATED APPLICATIONS

The present application claims priority to U.S. provisional application No. 63/036,561 filed Jun. 9, 2020, which is incorporated by reference in its entirety.

FIELD

The present application relates in general to prostacyclins and more particularly, to prodrugs of treprostinil and to methods of making and using such prodrugs.

SUMMARY

One embodiment is a compound of formula 5a or 5b:

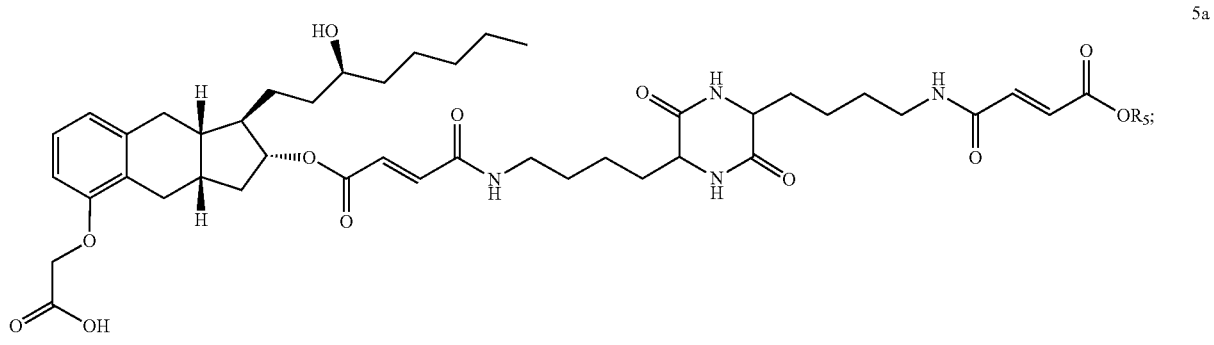

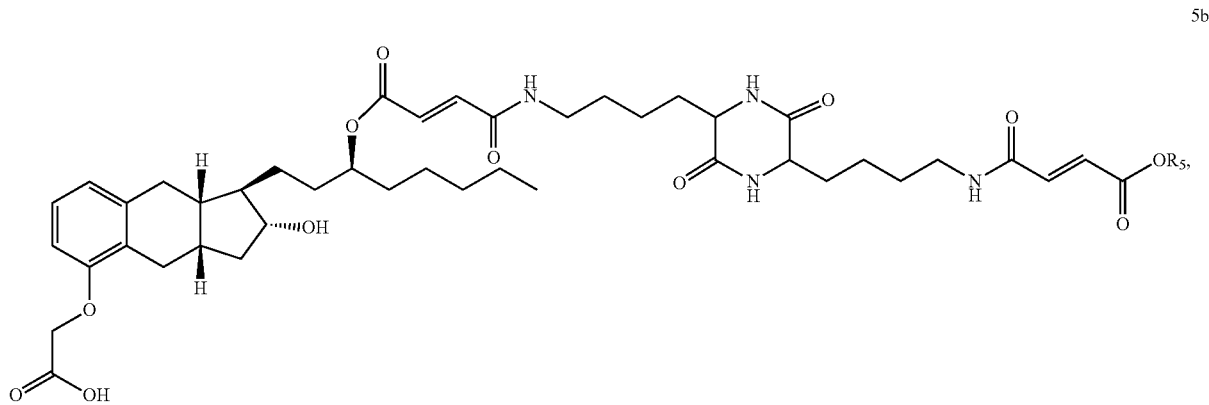

or a pharmaceutically acceptable salt thereof, wherein $R_5$ is H or a polymeric carrier.

Another embodiment is a pharmaceutically acceptable batch comprising a compound of the foregoing embodiment having a purity of at least 90%. Another embodiment is a pharmaceutical composition comprising a compound of the foregoing embodiment.

Another embodiment is a method of making an FDKP-treprostinil compound comprising:

i) double-protecting treprostinil (1)

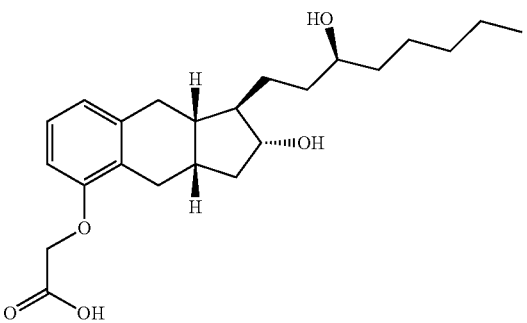 [SMILES: CCCCC[C@H](O)CC[C@@H]1[C@H]2Cc3cccc(OCC(=O)O)c3C[C@H]2C[C@H]1O]

to form a double-protected treprostinil moiety (2)

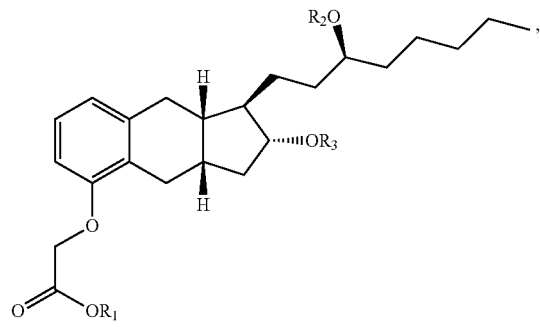

wherein R₁ is a carboxylic acid protecting group and wherein a) $R_2$ is H and $R_3$ is a hydroxyl protecting group or b) $R_2$ is a hydroxyl protecting group and $R_3$ is H;
ii) reacting the double-protected treprostinil moiety with a compound of formula (3)
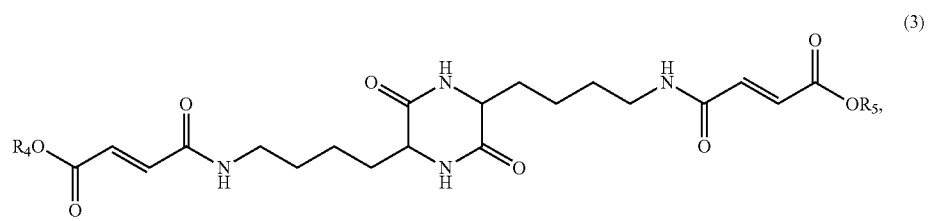
(3)
wherein $R_4$ is H,
to form a double-protected FDKP-treprostinil compound having formula (4a) or (4b); and
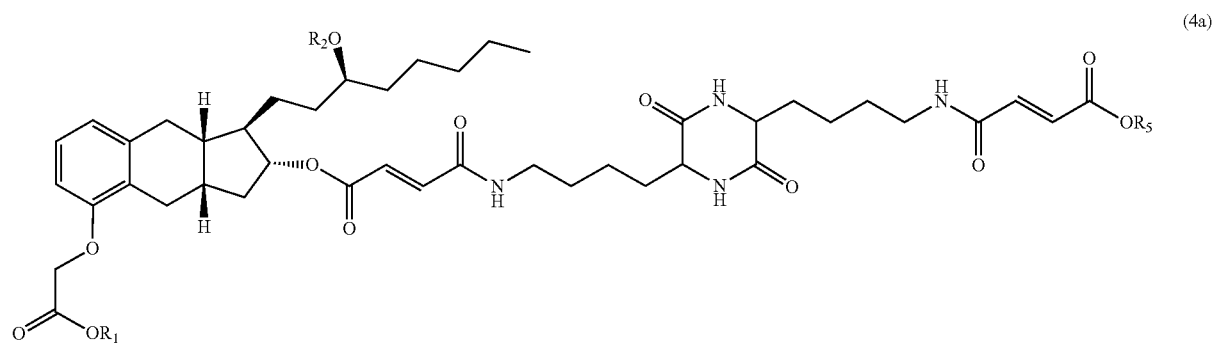
(4a)
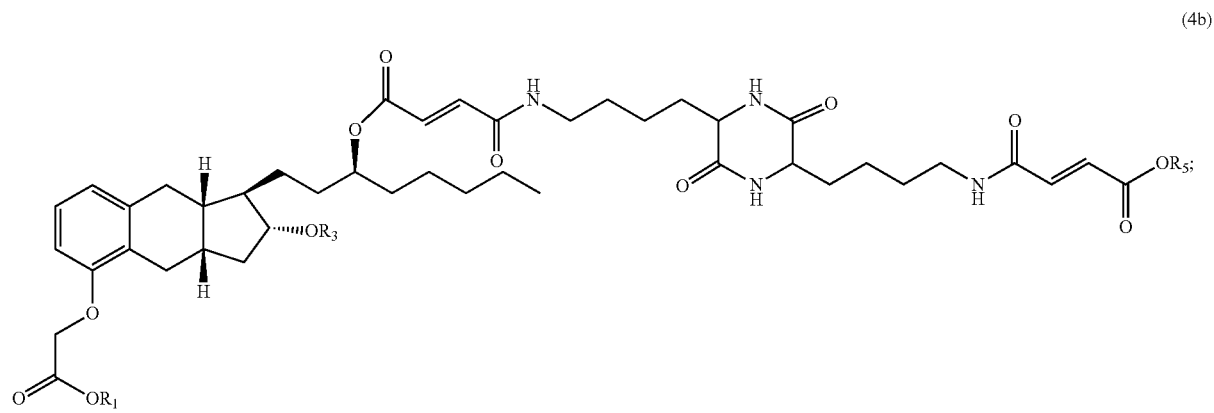
(4b)

and iii) deprotecting the double-protected FDKP-treprostinil compound to form an FDKP-treprostinil compound having formula (5a) or (5b)

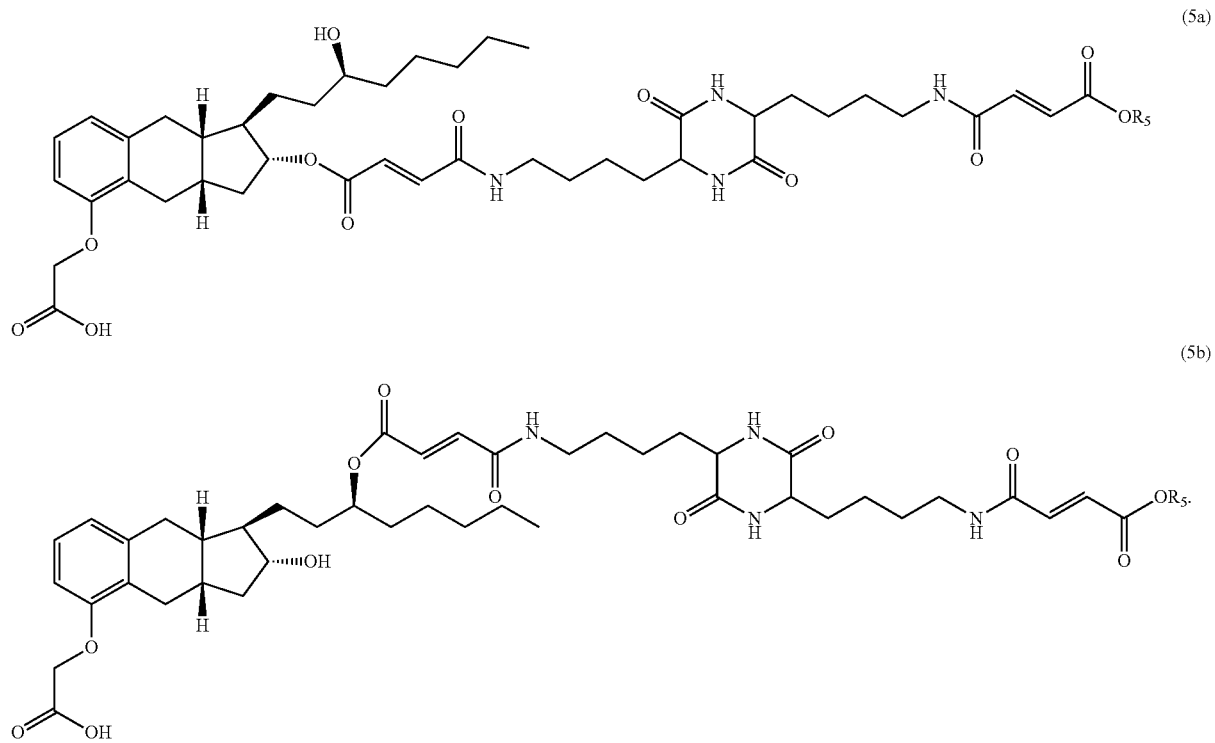

Another embodiment, is a method of treating a treprostinil-treatable condition comprising administering to a subject in need thereof a compound of the foregoing embodiment.

DETAILED DESCRIPTION

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively. The term "or" is inclusive unless modified, for example, by "either." Thus, unless context or an express statement indicates otherwise, the word "or" means any one member of a particular list and also includes any combination of members of that list. Other than in the examples, or where otherwise indicated, all numbers expressing quantities of ingredients or reaction conditions used herein should be understood as modified in all instances by the term "about."

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only and is not intended to limit the scope of the present invention, which is defined solely by the claims. In order that the present disclosure can be more readily understood, certain terms are first defined. Additional definitions All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art and are set forth throughout the detailed description.

"HPLC" refers to high-performance liquid chromatography.

"NMR" refers to nuclear magnetic resonance.

"FDKP" refers to fumaryl 2,5-diketopiperazine or (E)-3,6-bis[4-(N-carbonyl-2-propenyl)amidobutyl]-2,5-diketopiperazine.

"RRT" refers to a relative retention time.

"TMSE" refers to trimethylsilylethyl ester.

"TMBDS" refers to tert-butyldimethylsilyl.

"EDCI" refers to 1-ethyl-3-(3-dimethylaminopropyl)carbodiimide.

"DMAP" refers to 4-dimethylaminopyridine.

"DMA" refers to N, N-dimethylacetamide.

"DMF" refers to N,N-dimethylformamide.

"DMSO" refers to dimethyl sulfoxide.

"TBAF" refers to tetra-n-butylammonium fluoride.

"THF" refers to tetrahydrofuran.

"LCMS" refers to liquid chromatography mass spectroscopy.

"IR" refers to infrared spectroscopy.

"TFA" refers to trifluoroacetic acid.

"DIEA" or "DIPEA" refers to N,N-diisopropylethylamine.

"DQF-COSY" refers to double quantum filtered correlation spectroscopy.

"ACN" refers to acetonitrile.

"HOBt" refers to hydroxybenzotriazole.

"DEPT-NMR" refers to Distortionless Enhancement by Polarization Transfer Nuclear Magnetic Resonance.

As used herein, "protecting group" or "protective group" is used as known in the art and as demonstrated in T. W. Green, P. G. M. Wuts, Protective Groups in Organic Synthesis, Wiley-Interscience, New York, 1999 (hereinafter "Greene, Protective Groups in Organic Synthesis"), which is incorporated herein by reference in its entirety for its teachings relating to protective groups.

As used herein, "hydroxyl protective group" or "hydroxyl protecting group" refers to the generally understood definition of an alcohol or hydroxyl protecting group as defined in T. W. Green, P. G. M. Wuts, Protective Groups in Organic Synthesis, Wiley-Interscience, New York, 1999.

As used herein, "carboxylic acid protecting group," "carboxyl protecting group," "carboxylic acid protective group," "carboxyl protective group" refers to the generally understood definition of a carboxyl protecting group as defined in T. W. Green, P. G. M. Wuts, Protective Groups in Organic Synthesis, Wiley-Interscience, New York, 1999.

As used herein, $C_m$-$C_n$, such as $C_1$-$C_{12}$, $C_1$-$C_8$, or $C_1$-$C_6$, when used before a group refers to that group containing m to n carbon atoms.

"Optionally substituted" refers to a group selected from that group and a substituted form of that group. Substituents may include any of the groups defined below. In one embodiment, substituents are selected from $C_1$-$C_{10}$ or $C_1$-$C_6$ alkyl, substituted $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, substituted $C_2$-$C_6$ alkenyl, substituted $C_2$-$C_6$ alkynyl, substituted $C_6$-$C_{10}$ aryl, substituted $C_3$-$C_8$ cycloalkyl, substituted $C_2$-$C_{10}$ heterocyclyl, substituted $C_1$-$C_{10}$ heteroaryl, halo, nitro, cyano, —$CO_2H$ or a $C_1$-$C_6$ alkyl ester thereof.

"Pharmaceutically acceptable salt" refers to salts of a compound, which salts are suitable for pharmaceutical use and are derived from a variety of organic and inorganic counter ions well known in the art. Pharmaceutically acceptable salts include, when the compound contains an acidic functionality, by way of example only, sodium, potassium, calcium, magnesium, ammonium, and tetraalkylammonium. When the molecule contains a basic functionality, salts of organic or inorganic acids, such as hydrochloride, hydrobromide, tartrate, mesylate, acetate, maleate, and oxalate. Stahl and Wermuth, eds., "Handbook of Pharmaceutically Acceptable Salts," (2002), Verlag Helvetica Chimica Acta, Zürich, Switzerland), which is hereby incorporated by reference for its teachings related to pharmaceutically acceptable salts, discusses a variety of pharmaceutical salts, their selection, preparation, and use.

"Pulmonary hypertension" refers to all forms of pulmonary hypertension, WHO Groups 1-5. Pulmonary arterial hypertension, also referred to as PAH, refers to WHO Group 1 pulmonary hypertension. PAH includes idiopathic, heritable, drug- or toxin-induced, and persistent pulmonary hypertension of the newborn (PPHN).

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4 chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

Treprostinil, the active ingredient in Remodulin® (treprostinil) Injection, Tyvaso® (treprostinil) Inhalation Solution, and Orenitram® (treprostinil) Extended-Release Tablets, was described in U.S. Pat. No. 4,306,075. Methods of making treprostinil and other prostacyclin derivatives are described, for example, in Moriarty, et al., *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117, 8,461,393, 8,481,782; 8,242,305, 8,497,393, 8,940,930, 9,029,607, 9,156,786 and 9,388,154 9,346,738; U.S. Published Patent Application Nos. 2012-0197041, 2013-0331593, 2014-0024856, 2015-0299091, 2015-0376106, 2016-0107973, 2015-0315114, 2016-0152548, and 2016-0175319; PCT Publication No. WO2016/0055819 and WO2016/081658.

Various uses and/or various forms of treprostinil are disclosed, for examples, in U.S. Pat. Nos. 5,153,222, 5,234, 953, 6,521,212, 6,756,033, 6,803,386, 7,199,157, 6,054,486, 7,417,070, 7,384,978, 7,879,909, 8,563,614, 8,252,839, 8,536,363, 8,410,169, 8,232,316, 8,609,728, 8,350,079, 8,349,892, 7,999,007, 8,658,694, 8,653,137, 9,029,607, 8,765,813, 9,050,311, 9,199,908, 9,278,901, 8,747,897, 9,358,240, 9,339,507, 9,255,064, 9,278,902, 9,278,903, 9,758,465; 9,422,223; 9,878,972; 9,624,156; U.S. Published Patent Application Nos. 2009-0036465, 2008-0200449, 2008-0280986, 2009-0124697, 2014-0275616, 2014-0275262, 2013-0184295, 2014-0323567, 2016-0030371, 2016-0051505, 2016-0030355, 2016-0143868, 2015-0328232, 2015-0148414, 2016-0045470, 2016-0129087, 2017-0095432; 2018-0153847 and PCT Publications Nos. WO00/57701, WO20160105538, WO2016038532, WO2018/058124.

Treprostinil has the following chemical formula:

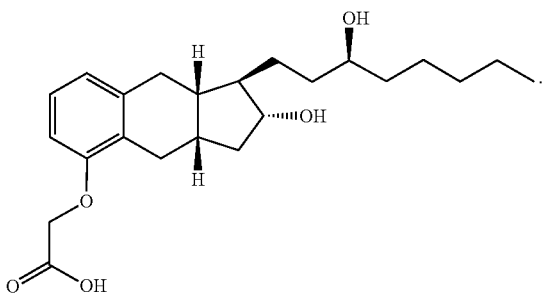 [SMILES: CCCCC[C@H](O)CC[C@@H]1[C@H]2Cc3cccc(OCC(=O)O)c3C[C@H]2C[C@H]1O]

The present inventors developed treprostinil prodrugs, which are compounds of formula (5a) or (5b):

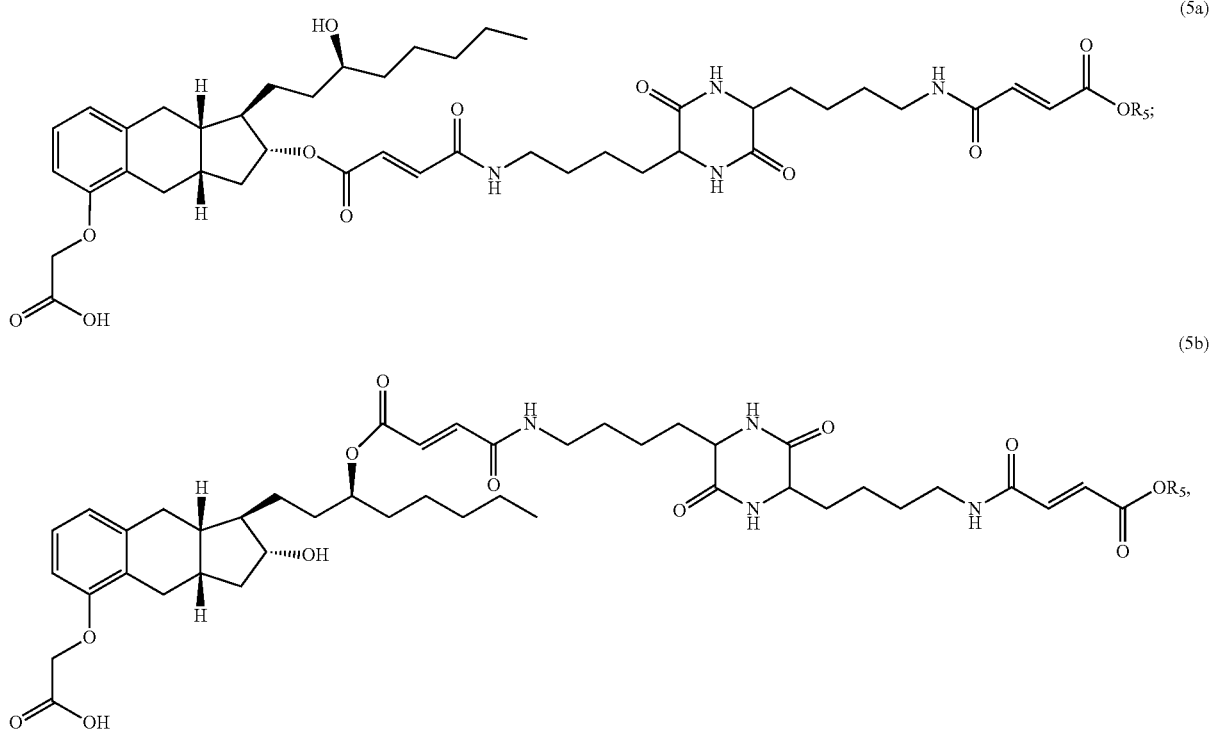

or their pharmaceutically acceptable salts. In formula (5a) and (5b), $R_5$ is H or a polymeric carrier, such as a polyethylene glycol (PEG) carrier, a fatty alcohol carrier, or a fatty amine carrier.

In some embodiments, the polymeric carrier, such as a PEG carrier, may have an average molecular weight, such as a number average molecular weight, from about 200 to about 200,000. In some embodiments, the polymeric carrier, such as a PEG carrier, may have an average molecular weight, such as a number average molecular weight, from about 200 to about 80000. In some embodiments, the polymeric carrier may be PEG 1500, PEG 4000, PEG 5000, PEG 8000, PEG 10,000, PEG 15,000, PEG 20,000 and PEG 25,000. In some embodiments, the polymeric carrier may be PEG 20,000.

In some embodiments, the fatty alcohol carrier comprises a $C_1$-$C_{20}$ alcohol. In some embodiments, the fatty alcohol carrier is saturated or unsaturated. In some embodiments, the fatty alcohol carrier is a saturated fatty alcohol carrier such as 1-hexanol, 1-heptanol, 1-octanol, 1-nonanol, 1-decanol, etc. In some embodiments, the fatty alcohol carrier is an unsaturated fatty alcohol carrier such as 10-undecen-1-ol, (Z)-9-octadecen-1-ol, (E)-9-octadecen-1-ol, (Z,Z)-9,12-octadecadien-1-ol, etc. Other fatty alcohols known in the art may be used as the fatty alcohol carrier, for example, those disclosed in K. Nowek et al., (2012) 'Fatty Alcohols' in *Ullmann's Encyclopedia of Industrial Chemistry*. Wiley-VCH Verlag GmbH & Co. KGaA, which is hereby incorporated in its entirety for its teaching of fatty alcohols.

In some embodiments, $R_5$ is a fatty amine carrier and forms an amide bond with the carboxyl group. In some embodiments, the fatty amine carrier comprises a $C_1$-$C_{20}$ amine. In some embodiments, the fatty amine carrier is saturated or unsaturated. In some embodiments, the fatty amine carrier is a saturated fatty amine carrier such as 1-hexanamine, 1-heptanamine, 1-octanamine, 1-nonanamine, 1-decanamine, etc. In some embodiments, the fatty amine carrier is an unsaturated fatty amine carrier such as 10-undecen-1-amine, (Z)-9-octadecen-1-10-undecen-1-amine, (E)-9-octadecen-1-10-undecen-1-amine, (Z,Z)-9,12-octadecadien-1-10-undecen-1-amine, etc. Other fatty amines known in the art may be used as the fatty amine carrier, for example, those disclosed in K. Eller et al., (2012) 'Fatty Amines' in *Ullmann's Encyclopedia of Industrial Chemistry*. Wiley-VCH Verlag GmbH & Co. KGaA, which is hereby incorporated in its entirety for its teaching of fatty amines.

When administered to a subject, such as a human being, the prodrug may undergo an in vivo biotransformation through, for example, a chemical cleavage or an enzymatic cleavage allowing a delivery of an effective amount of treprostinil to the subject.

Pharmaceutical Compositions

Treprostinil prodrugs may be provided in a form of a pharmaceutical composition, which may also comprise a pharmaceutically acceptable carrier, excipient, binder, diluent or the like. Such pharmaceutical composition may be manufactured by methods known in the art such as granulating, mixing, dissolving, encapsulating, lyophilizing, emulsifying or levigating processes, among others. The composition may be in the form of, for example, granules, powders, tablets, capsules, syrup, suppositories, injections, emulsions, elixirs, suspensions and solutions. The composition may be formulated for a number of different administration routes, such as, for oral administration, transmucosal administration, rectal administration, transdermal or subcutaneous administration, as well as intrathecal, intravenous, intramuscular, intraperitoneal, intranasal, intraocular or intraventricular injection. The treprostinil prodrug may be administered by any of the above routes, for example in a local rather than a systemic administration, including as an injection or as a sustained release formulation.

In some embodiments, the treprostinil prodrug can be administered by inhalation. The treprostinil can be formulated for dry powder inhalation (DPI) using any suitable technology or formulation.

In one embodiment, the pharmaceutical composition can compromise a prodrug of treprostinil and a carrier, such as sterile water. In some embodiments, the prodrug of treprostinil is formulated for subcutaneous administration, and such formulation may or may not include m-cresol or another preservative.

For oral, buccal, and sublingual administration, powders, suspensions, granules, tablets, pills, capsules, gelcaps, and caplets may be acceptable as solid dosage forms. These can be prepared, for example, by mixing one or more treprostinil prodrugs, or pharmaceutically acceptable salts thereof, with at least one additive or excipient such as a starch or other additive. Suitable additives or excipients may be sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms may contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers. Besides those representative dosage forms described above, pharmaceutically acceptable excipients and carriers are generally known to those skilled in the art and can be employed. Such excipients and carriers are described, for example, in "Remingtons Pharmaceutical Sciences" Mack Pub. Co., New Jersey (1991), which is incorporated herein by reference.

A treprostinil prodrug may be formulated in a formulation suitable for parenteral administration that may comprise sterile aqueous preparations of a treprostinil prodrug, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations may contain from 0.1 to 5% w/v based on weight of treprostinil in the prodrug and may be administered at a rate of 0.1 ml/min/kg. Alternatively, the prodrug may be administered at a rate of 0.625 to 50 ng/kg/min based on weight of treprostinil in the prodrug. Alternatively, the prodrug may be administered at a rate of 10 to 15 ng/kg/min based on weight of treprostinil in the prodrug.

In some embodiments, a concentration of a treprostinil prodrug in a formulation for parenteral administration, such as intravenous infusion or subcutaneous infusion (including continuous subcutaneous infusion), may be from 0.0005 to 30 mg/mL or from 0.0007 to 50 mg/mL or from 0.001 to 15 mg/mL or any value or subrange within these ranges. Exemplary concentrations may include 0.1 mg/mL, 1 mg/mL, 2.5 mg/mL, 5 mg/mL or 10 mg/mL.

In some embodiments, a formulation of a treprostinil prodrug for parenteral administration, such as intravenous infusion or subcutaneous infusion (including continuous subcutaneous infusion), may be prepared by admixing the prodrug with a vehicle, such as a buffer. In certain embodiments, the vehicle may be a phosphate containing vehicle, i.e. at least one phosphate salt, which may be for example, dibasic phosphate, such as sodium dibasic phosphate or potassium dibasic phosphate, or tribasic phosphate, such as sodium tribasic phosphate or potassium phosphate. In certain embodiments, the vehicle may also contain a halogen salt, such as a chloride salt, which may be, for example, sodium chloride or potassium chloride. The halogen salt, such as sodium chloride may be used to adjust tonicity of the vehicle. In certain embodiments, it may be preferred that a phosphate and a halogen salt have the same cation. For example, when a phosphate is sodium phosphate, such as sodium tribasic phosphate or sodium tribasic phosphate, a halogen salt may a sodium halogen salt such as sodium chloride. Similarly, when a phosphate is potassium phosphate, such as potassium tribasic phosphate or potassium tribasic phosphate, a halogen salt may a potassium halogen salt such as potassium chloride. A solvent in the vehicle may contain water. In certain embodiments, water may be the only solvent in the vehicle. Yet in certain embodiments, the vehicle may contain one or more additional solvent in addition to water. In some embodiments, an additional solvent may be a preservative, such as m-cresol.

Preferably, the vehicle is isotonic with blood of a patient, such as a human being. The term isotonic may mean that the osmolarity and ion concentrations of the vehicle match those of the patient, such as human being. Non-limiting example of vehicles include phosphate-buffered saline, which is a water-based salt solution containing disodium hydrogen phosphate, sodium chloride and, in some formulations, potassium chloride and potassium dihydrogen phosphate. Other examples may include a vehicle containing 20 mM disbasic sodium phosphate with 125 mM sodium chloride and a vehicle containing 15 mM sodium phosphate tribasic, 125 mM sodium chloride and 0.3% w/w m-cresol.

Methods of Treatment

The treprostinil prodrugs can be used to treat a treprostinil treatable disease or condition, i.e., a disease or condition against which treprostinil is known to be effective. In some embodiments, such condition may be pulmonary hypertension. In some embodiments, the treprostinil prodrugs can be used to treat pulmonary arterial hypertension (PAH). In some embodiments, the treprostinil prodrugs can be used to treat one or more of WHO Groups 1-5 pulmonary hypertension. Likewise, the treprostinil prodrugs described herein can be used to treat any disease or condition for which treprostinil is indicated or useful. The treprostinil prodrugs can be administered as the sole therapeutic agent or in addition to other active agents, including treprostinil.

In some embodiments, a method of treating a disease or condition is provided, the method comprising administering to a subject a compound (e.g., a prodrug) or composition disclosed herein. In some embodiments, the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis, and asthma. In some embodiments, the disease is pulmonary hypertension.

Administration may be performed via a route described above, or, for example, orally, intravenously, intra-arterial, intramuscularly, intranasally, rectally, vaginally, or subcutaneously. In some embodiments, the composition is administered by an injection. In some embodiments, the administering is performed orally. In some embodiments, the administering is performed subcutaneously.

The subject treated may be a human, canine, feline, aves, non-human primate, bovine, or equine. In a preferred embodiment, the subject is a human.

In some embodiments, a method of treating a disease or condition is provided, the method comprising administering to a subject a prodrug of treprostinil, wherein upon said administering said prodrug converts to a metabolic product. The metabolic product can comprise, consist essentially of, or consist of treprostinil.

The treprostinil prodrug may be administered to a subject, such as a human being, in an effective amount.

The term "effective amount" may mean an amount of a treprostinil prodrug, which may be necessary to treat a disease or condition, such as pulmonary hypertension. In some embodiments, an effective amount of treprostinil prodrug may be the same or similar to an effective amount of treprostinil for treating the same disease or condition. In some embodiments, an effective amount of treprostinil prodrug may be different from an effective amount of treprostinil for treating the same disease or condition. A person of ordinary skill in the art would be able to determine and "effective amount" of the treprostinil prodrug based, for example, on the relevant disease or condition, the amount of treprostinil known to treat, ameliorate, or prevent the disease or condition, and the rate at which the prodrug converts to treprostinil in vivo.

Methods of Making

FDKP-treprostinil prodrugs may be prepared from a double-protected treprostinil moiety wherein the treprostinil moiety has two out of its three hydroxyl groups protected with hydroxyl protecting groups.

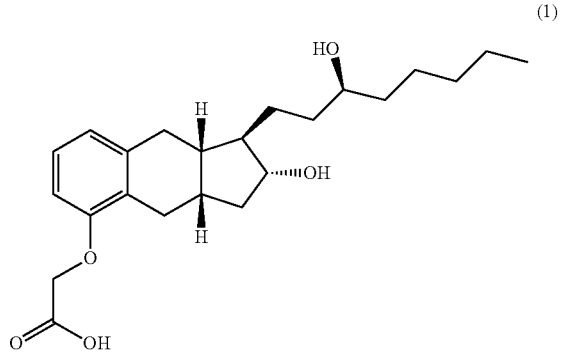 [SMILES: CCCCC[C@H](O)CC[C@@H]1[C@H]2Cc3cccc(OCC(=O)O)c3C[C@H]2C[C@H]1O]

(1)

The double-protected treprostinil moiety may be formed from unprotected treprostinil, i.e., compound of formula (1) using, for example, methods disclosed in Greene, Protective Groups in Organic Synthesis, which is incorporated herein by reference in its entirety.

For forming the cyclopentyl ring FDKP-treprostinil prodrug, the double protected treprostinil moiety may be a compound of formula (2a), while for forming the side chain FDKP-treprostinil prodrug, the double protected treprostinil moiety may be a compound of formula (2b).

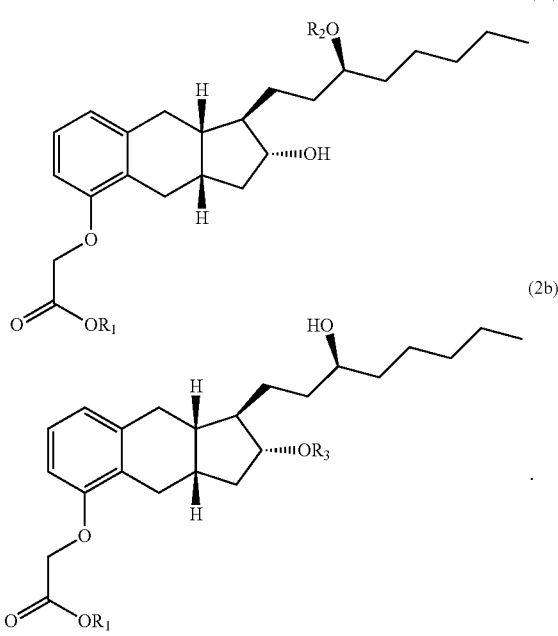

In some embodiments, in the double-protected treprostinil moiety, $R_1$ and $R_2$ (or $R_3$) is a protecting group. $R_1$ and $R_2$ (or $R_3$) may be the same or different. In some embodiments, $R_1$ may be a silyl carboxylic acid protecting group or a benzyl carboxylic acid protecting group. The silyl carboxylic acid protecting group may be, for example, trimethylsilyl, triethylsilyl, tri-iso-propylsilyloxymethyl, triisopropyl silyl, t-butyldimethylsilyl, t-butyldiphenylsilyl, phenyldimethylsilyl. The benzyl carboxylic acid protecting group may be unsubstituted benzyl or a substituted benzyl group, i.e., a benzyl group substituted at one or more meta, ortho or para positions with one or more substituents, which may be independently selected from the group consisting of —$NO_2$, —CN, halogen (e.g., —F, —Cl, —Br or —I), ($C_1$-$C_3$)alkyl, halo($C_1$-$C_3$)alkyl, ($C_1$-$C_3$)alkoxy and halo($C_1$-$C_3$)alkoxy. In some embodiments, $R_2$ (or $R_3$) may be a silyl hydroxyl protecting group, such as, for example, trimethylsilyl, triethylsilyl, tri-iso-propylsilyloxymethyl, triisopropyl silyl, t-butyldimethylsilyl, t-butyldiphenylsilyl, phenyldimethylsilyl.

The double-protected treprostinil moiety may be reacted with an FDKP moiety, such as a compound of formula (3), to form a double-protected FDKP-treprostinil compound, which may be a double-protected FDKP-treprostinil compound of formula (4a) or (4b)

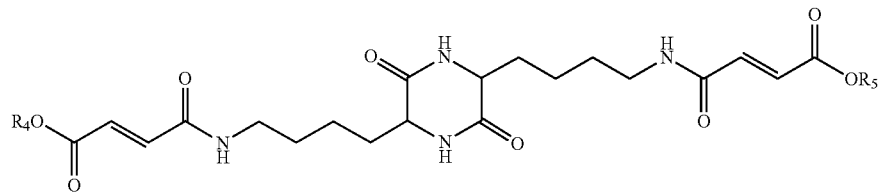

(3)

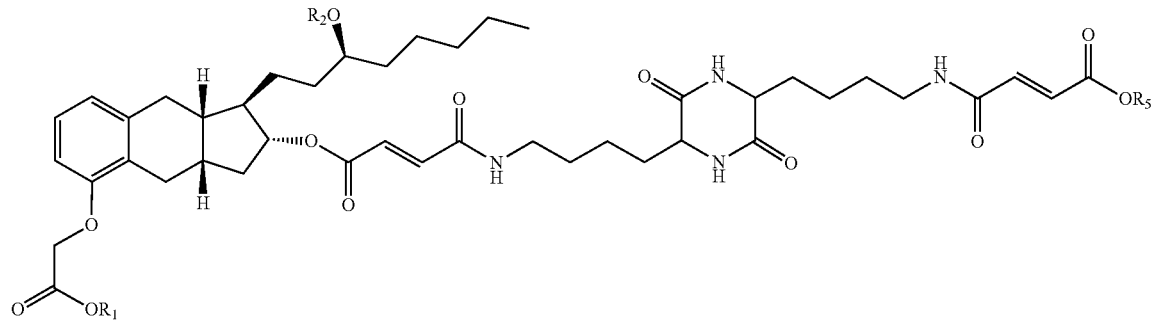

(4a)

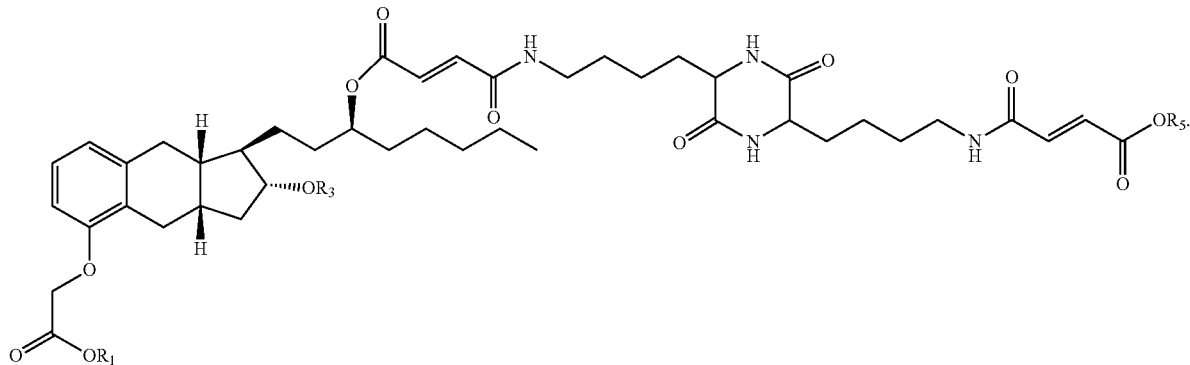

(4b)

In the FDKP moiety, $R_5$ may be H.

The coupling reaction between the FDKP moiety and the double protected treprostinil moiety may be performed in the presence of a carbodiimide, which may be a water soluble carbodiimide, such as EDCI. The reaction between the FDKP moiety and the double protected treprostinil moiety may be performed in the presence of a nucleophilic catalyst, which may be a pyridine compound, such as DMAP. In some embodiments, the nucleophilic catalyst, such DMAP, may be used together with an organic base, such as DIPEA or triethylamine. The nucleophilic catalyst, such as DMAP, alone or with an organic base may be in a polar solvent, such as DMA, DMF, DMSO or any combination thereof. The reaction between the FDKP moiety and the double protected treprostinil moiety may be performed in the presence of a coupling reagent selected from Table 1, below.

In a compound of formula (5a) or (5b), wherein $R_5$ is a polymeric carrier, a fatty alcohol carrier, or a fatty amine carrier, the compound may be formed from a coupling reaction of a compound of formula (5a) or (5b), wherein $R_5$ is H, and the polymer, fatty acid, or fatty amine. In some embodiments, the coupling is a dicyclohexyl carbodiimide (DCC) coupling or a coupling performed using a reagent selected from Table 1, below.

TABLE 1

Coupling Reagents

| Reagent | Full Name |
|---|---|
| BOP | (Benzotriazole-1-yl-oxy-tris-(dimethylamino)-phosphonium hexafluorophosphate) |
| COMU | (1-[1-(Cyano-2-ethoxy2-oxoethylideneaminooxy)-dimethylamino-morpholino]-uronium hexafluorophosphate) |
| DEPBT | (3-(Diethoxy-phosphoryloxy)-1,2,3-benzo[d]triazin-4(3H)-one) |
| EEDQ | (N-Ethoxycarbonyl-2-ethoxy-1,2-dihydroquinoline) |
| HATU | (N-[(7-Aza-1H-benzotriazol-1-yl) (dimethylamino)-methylene]-Nmethylmethanaminium hexafluorophosphate N-oxide) |
| HDMC | (N-[(5-Chloro-1H-benzotriazol-1-yl)-dimethylamino-morpholino]-uronium hexafluorophosphate N-oxide) |
| PyBOP | (Benzotriazol-1-yloxy-tripyrrolidinophosphonium hexafluorophosphate) |
| PyOxim | ((Ethyl cyano(hydroxyimino)acetatoO2)-tri-(1-pyrrolidinyl)-phosphonium hexafluorophosphate) |
| TATU | (N-[(7-Aza-1H-benzotriazol-1-yl) (dimethylamino)-methylene]-Nmethylmethanaminium tetrafluoroborate N-oxide) |
| TBTU | (N-[(1H-Benzotriazol-1-yl) (dimethylamino)-methylene]-Nmethylmethanaminium tetrafluoroborate N-oxide) |
| TFFH | (Tetramethylfluoroformamidinium hexafluorophosphate) |
| TOTT | (2-(1-Oxy-pyridin-2-yl)-1,1,3,3-tetramethylisothiouronium tetrafluoroborate) |

The double-protected FDKP-treprostinil moiety may be deprotected to form an unprotected FDKP-treprostinil compound of formula (5a) or (5b).

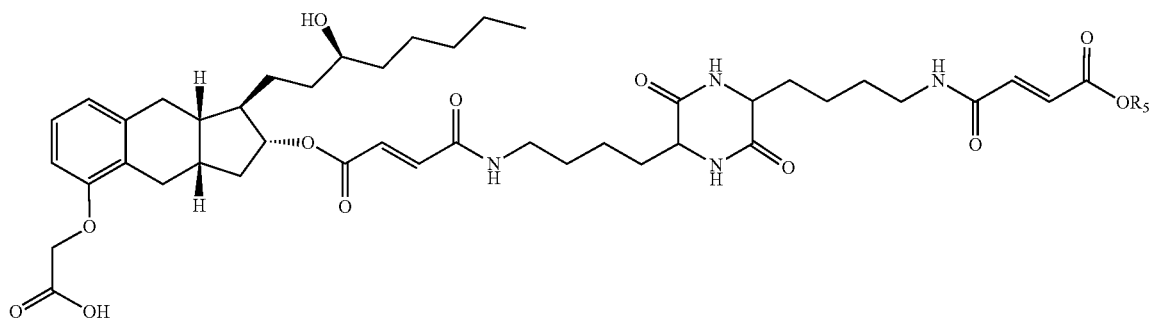

(5a)

(5b)

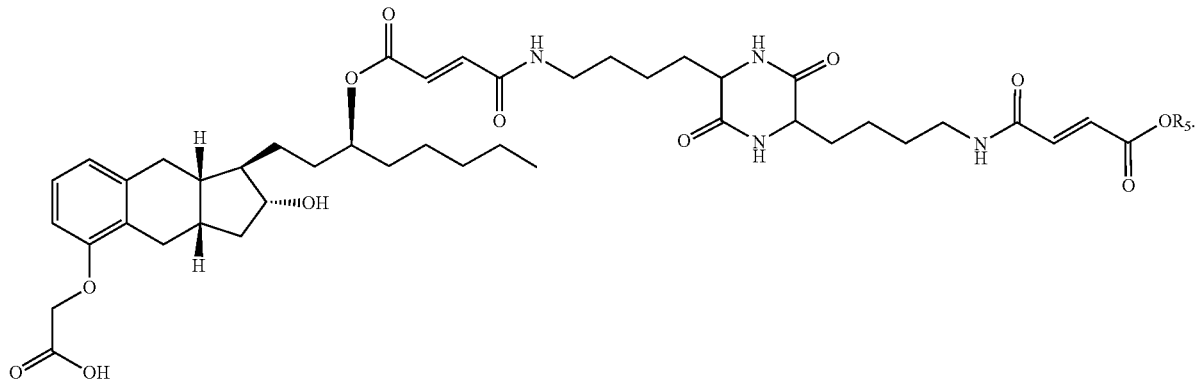

In some embodiments, the deprotection of the double-protected FDKP-treprostinil compound of formula 4a(4b) may be performed in one step by cleaving protecting groups at $R_1$ and $R_2(R_3)$ in one step and replacing them with hydrogen. For example, protecting groups at $R_1$ and $R_2(R_3)$ are the same type of protecting groups and the deprotection of the double-protected FDKP-treprostinil compound of formula 4a(4b) may be performed in one step. For example, when protecting groups at $R_1$ and $R_2(R_3)$ are both silyl protecting groups, which may or may not be the same, the deprotection of the double protected FDKP-treprostinil compound of formula 4a(4b) may be performed in one step using a silyl ester or ether cleaving agent, which may be an acid or a fluoride, such as tetra-n-butylammonium fluoride.

Yet in some embodiments, the deprotection of the double-protected FDKP-treprostinil compound of formula 4a(4b) may be performed in two steps: one for cleaving the carboxyl protecting groups at $R_1$ and the other for cleaving the hydroxyl protecting groups at $R_2(R_3)$. In some embodiments, the cleavage may be first performed for $R_1$ and then for $R_2(R_3)$. In some other embodiments, the cleavage may be first performed for $R_2(R_3)$ and then for $R_1$. For example, when $R_1$ is a benzyl carboxylic acid protecting group and $R_2$ (or $R_3$) is a silyl hydroxyl protecting group, such as trimethylsilyl, triethylsilyl, tri-iso-propylsilyloxymethyl, triisopropyl silyl, t-butyldimethylsilyl, or t-butyldiphenylsilyl, phenyldimethylsilyl, the benzyl carboxylic acid protecting group may be cleaved at $R_1$ to form a single-protected FDKP-treprostinil compound of formula (6a) or (6b):

(6a)

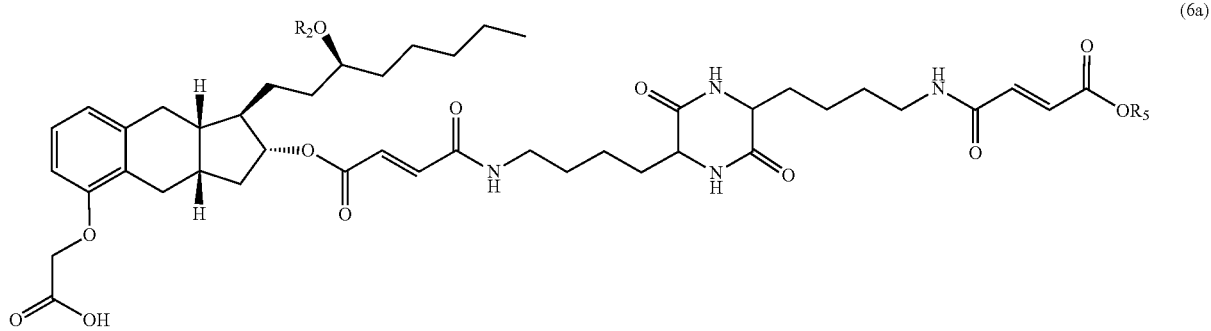

(6b)

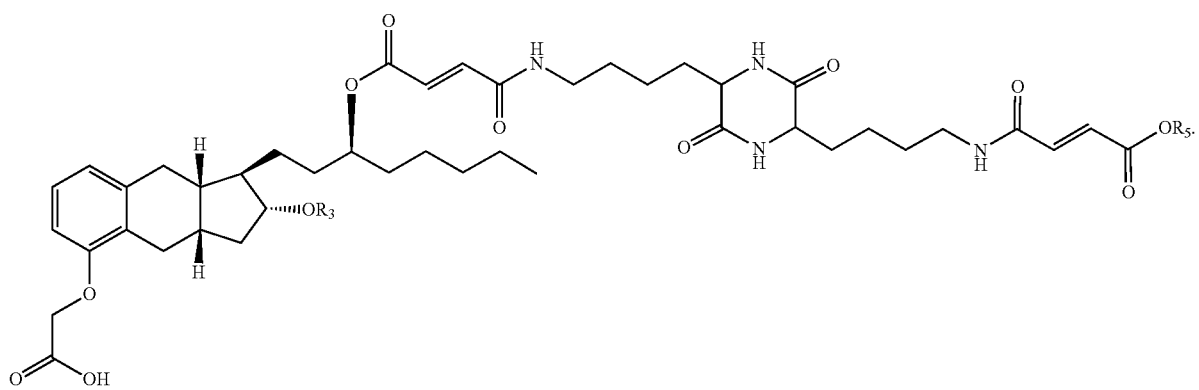

The cleavage of the benzyl carboxylic acid protecting group at $R_1$ may be performed using a chemoselective benzyl cleavage agent, such as trimethyltin hydroxide, barium hydroxide, barium carbonate, cesium hydroxide, cesium carbonate, other alkali metal hydroxides and carbonates, tributyltin hydroxide, tetramethylammonium hydroxide or tetrabutyl ammonium hydroxide.

The unprotected FDKP-treprostinil compound of formula (5a) or (5b) may be then formed from the single-protected FDKP-treprostinil compound of formula (6a) or (6b). In some embodiments, the unprotected FDKP-treprostinil compound of formula (5a) or (5b) may be formed from the single protected FDKP-treprostinil compound of formula (6a) or (6b) by cleaving the silyl ether hydroxyl protecting group at $R_2$ or $R_3$ by using a silyl ether cleaving agent, which may be an acid or a fluoride, such as tetra-n-butylammonium fluoride. Yet in some other embodiments, the unprotected FDKP-treprostinil compound of formula (5a) or (5b) may be formed from the single protected FDKP-treprostinil compound of formula (6a) or (6b) by simply storing the single protected FDKP-treprostinil compound of formula (6a) or (6b) for an extended period of time, such as at least 10 hours or at least 12 hours or at least 14 hours or at least 16 hours or at least 18 hours, to allow cleaving of the silyl ether hydroxyl protecting group at $R_2$ or $R_3$, with a silyl ether cleaving agent, which may be an acid or a fluoride, such as tetra-n-butylammonium fluoride. For example, in some embodiments, storing the single protected FDKP-treprostinil compound of formula (6a) or (6b) for an extended period of time, such as at least 10 hours or at least 12 hours or at least 14 hours or at least 16 hours or at least 18 hours, with a low concentration, such as from about 0.005% to about 0.2% or from about 0.01% to about 0.1%, of trifluoroacetic acid (TFA) may allow cleaving of the silyl ether hydroxyl protecting group at $R_2$ or $R_3$.

The FDKP-treprostinil compound of formula (5a) or (5b) may be produced with a batch with a purity of at least 90% or at least 92% or at least 93% or at least 94% or at least 95% or at least 96% or at least 97% or at least 98% or at least 98.5%. In some embodiments, a group of batches has an average purity of at least 90% or at least 92% or at least 93% or at least 94% or at least 95% or at least 96% or at least 97% or at least 98% or at least 98.5%.

In some embodiments, a batch of the compound of formula (5a) may be substantially free of the compound of formula (5b). In some embodiments, a batch of the compound of formula (5b) may be substantially free of the compound of formula (5a). For example, in some embodiments, a batch of the compound of formula (5a) may contain less than 5% or less than 4% or less than 3% or less than 2% or less than 1% or less than 0.5% or less than 0.3% or less than 0.1% of the compound of formula (5b). Similarly, in some embodiments, a batch of the compound of formula (5b) may contain less than 5% or less than 4% or less than 3% or less than 2% or less than 1% or less than 0.5% or less than 0.3% or less than 0.1% of the compound of formula (5a).

An amount of the compound of formula (5a) or (5b) in a batch may be, for example, at least 0.1 g, at least 0.3 g, at least 0.5 g, at least 0.8 g, at least 1 g, at least 1.2 g, at least 1.5 g, at least 2 g, at least 3 g, at least 4 g or at least 5 g.

Embodiments described herein are further illustrated by, though in no way limited to, the following working examples.

EXAMPLES

Example 1

Treprostinil prodrugs with (E)-3,6-bis[4-(N-carbonyl-2-propenyl)amidobutyl]-2,5-diketopiperazine (FDKP) were synthesized. Specifically, FDKP-treprostinil cyclopentil ring ester and FDKP-treprostinil side chain ester were synthesized as shown in Scheme 1 and Scheme 2, respectively.

Scheme 1: Synthesis of FDKP-Treprostinil Cyclopentyl Ring Ester (6)

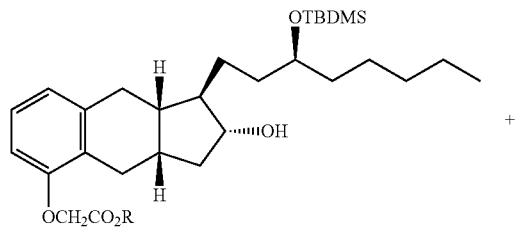

1, R = TMSE (CH$_2$CH$_2$SiMe$_3$)
2, R = Benzyl

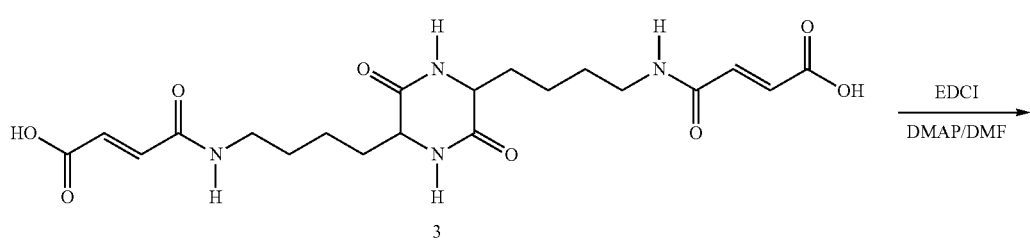

3

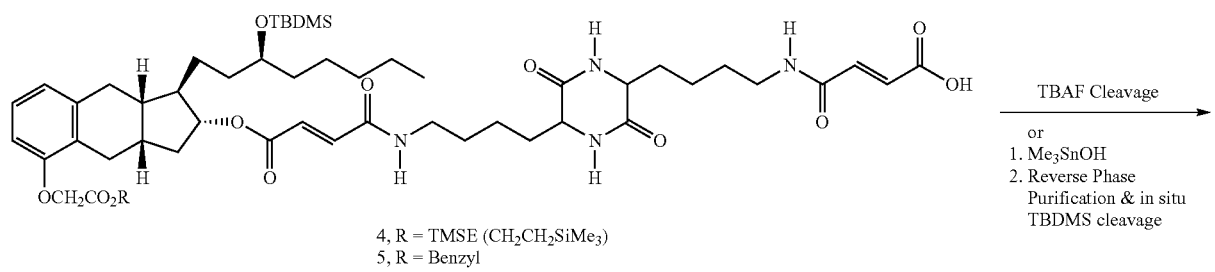
4, R = TMSE (CH$_2$CH$_2$SiMe$_3$)
5, R = Benzyl
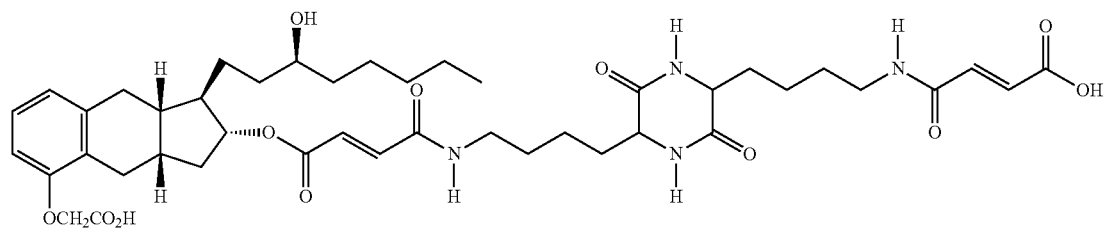
6
Scheme 2: Synthesis of FDKP-Treprostinil Side Chain Ester (9)
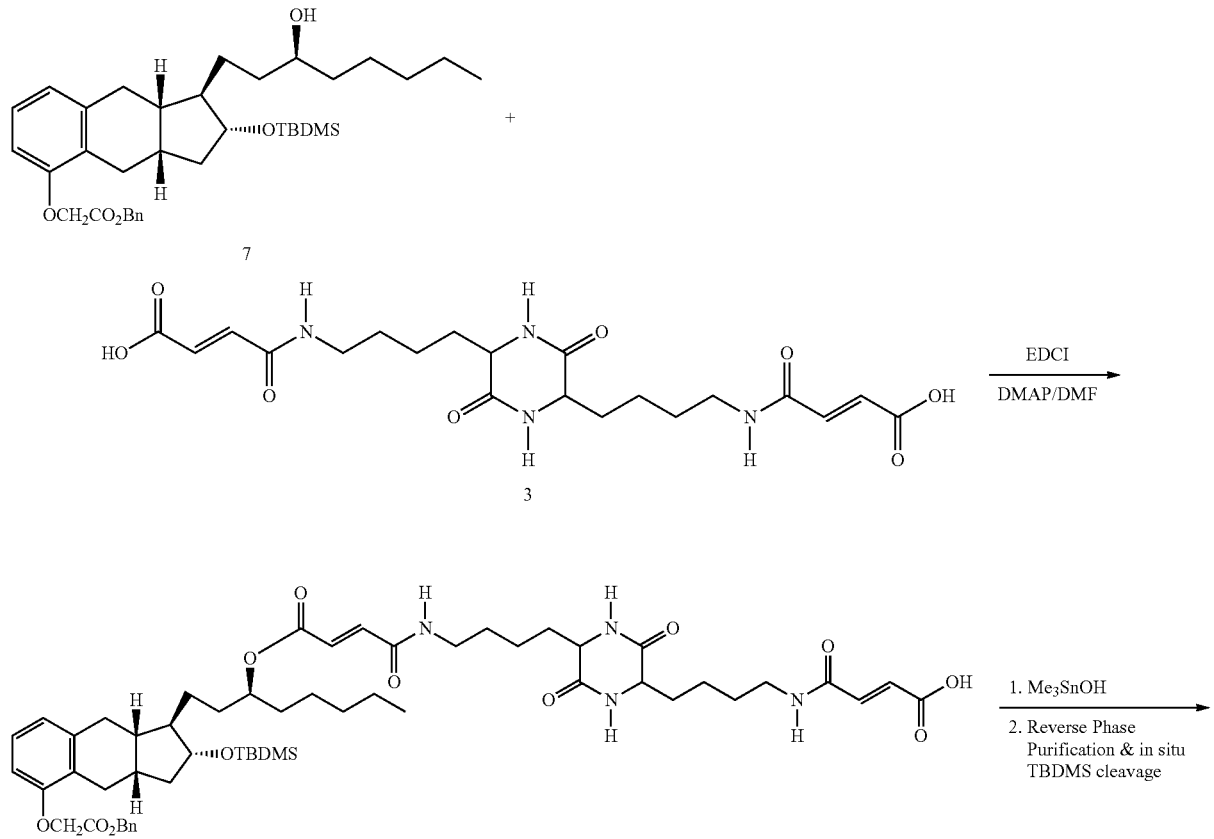

-continued

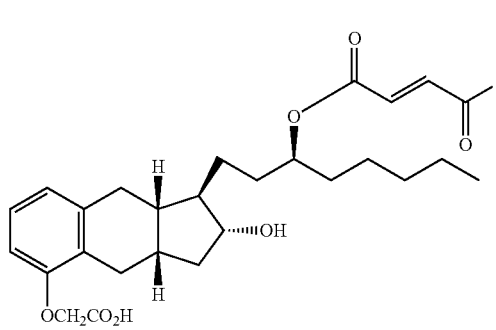 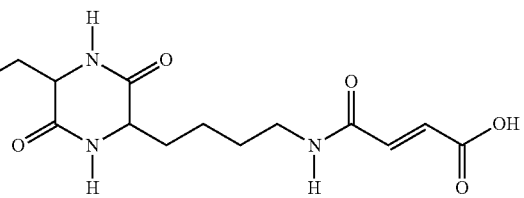

9

FDKP-Treprostinil Esters: The diprotected treprostinil moiety, side chain TBDMS treprostinil TMSE ester (1, R=TMSE) was coupled with (E)-3,6-bis[4-(N-carbonyl-2-propenyl)amidobutyl]-2,5-diketopiperazine (FDKP) (3) in the presence of EDCI·HCl and DMAP in DMA or DMF or DMSO to give mono-TBDMS FDKP treprostinil TMSE cyclopentyl ring ester (4, R=TMSE) in modest yield after chromatographic separation on reverse phase pre-packed column using water and acetonitrile. Attempted desilylation of TMSE and TBDMS groups from 4 using TBAF in THF gave some desired product, FDKP treprostinil cyclopentyl ring ester (6) along with FDKP cleaved product, i.e treprostinil. To overcome the FDKP cleavage during desilylation, the protecting group, TMSE was replaced by benzyl group in the protection of acid. The benzyl protected acid, side chain TBDMS treprostinil benzyl ester (2, R=benzyl) was used for the coupling reaction. The side chain TBDMS treprostinil benzyl ester (2) was coupled with FDKP to produce TBDMS FDKP treprostinil benzyl cyclopentyl ring ester (5, R=benzyl) after reverse phase column chromatography in modest yield and confirmed by LCMS and $^1$H NMR. The chemoselective debenzylation of crude (5, R=benzyl) with trimethyltin hydroxide in 1,2-dichloroethane afforded the corresponding acid (5, R=H). There was a trace of FDKP cleaved product. The purification of the crude acid by reverse phase column using 0.05% trifluoroacetic acid (TFA) in water and acetonitrile provided the desired FDKP-treprostinil cyclopentyl ring ester (6). The desilylation of TBDMS happened during the storage of the combined fractions in the refrigerator overnight due to the mildly acidic nature of the 0.05% TFA solution. This avoided an extra chemical step for the cleavage of TBDMS group to obtain final compound 6. The lyophilization of the combined fractions provided pure FDKP treprostinil cyclopentyl ring ester (6) as off-white solid and was characterized by IR, $^1$H NMR and LCMS. Under similar reaction condition, cyclopentyl TBDMS treprostinil benzyl ester (7) was also coupled with FDKP (2) to give TBDMS FDKP-treprostinil benzyl side chain ring ester (3). The chemoselective debenzylation of the crude product (8) with trimethyltin hydroxide followed by desilylation during reverse phase column chromatography afforded FDKP-treprostinil side chain ester (9) in modest yield and characterized by IR, $^1$H NMR and LCMS.

Synthetic Methods:

The coupling of diprotected treprostinil (1 or 2) with (E)-3,6-bis[4-(N-carbonyl-2-propenyl)amidobutyl]-2,5-diketopiperazine (FDKP) (3) using various coupling reagents were attempted:

EDCI·HCl, DMAP, DIEA in N,N-dimethylacetamide (DMA)

EDCI·HCl, DMAP in DMA or N,N-dimethylformamide (DMF) or dimethyl sulfoxide (DMSO)

O-(benzotriazole-1-yl)-N,N,N',N'-tetramethylurorium tetrafluoroborate (TBTU) and DBU in DMA 2-Chloro-1-methylpyridinium iodide (CMPI) and triethylamine in DMA EDCI·HCL, DMAP, HOBt, DIPEA in DMA Solid supported EDCI, solid supported DMAP in DMF.

The coupling reaction of diprotected treprostinil (1 or 2) with FDKP (3) using EDCI·HCl, DMAP in DMF or DMA or DMSO gave the desired coupled product (4 or 5) and other reagents did not work (Schemes 1 and 2). The compound (4) was purified by reverse phase column chromatography using acetonitrile and water as mobile phase. The attempted cleavage of TBDMS and TMSE from compound (4) using tetrabutylammonium fluoride (TBAF) afforded some desired compound (6) along with treprostinil (due to the cleavage of ester linkage), and the similar result was observed when compound (5) was used. Later, the TBAF was replaced by trimethyltin hydroxide to perform chemoselective cleavage of benzyl ester from compound (3b) to give corresponding acid. The hydrolysis of ester linkage between FDKP and treprostinil moiety was minimal when trimethyltin hydroxide was used. The purification of the crude acid after benzyl ester hydrolysis by reverse phase column chromatography using 0.05% TFA in water/0.05% TFA in ACN afforded the TBDMS FDKP-treprostinil-cyclopentyl ring ester, the precursor of compound (6). The desired product was detected by LCMS. There was a cleavage of TBDMS group during the storage of the purified product produced the final product (6). Lyophilization of the combined pure fractions afforded FDKP-treprostinil-cyclopentyl ring ester (6) as off-white solid. The pure compound (6) was characterized by IR, $^1$H NMR, DQF-COSY and LCMS.

After successful synthesis of FDKP-treprostinil-cyclopentyl ring ester (6), the similar reaction conditions were used to synthesize FDKP-treprostinil-side chain ester (9) using diprotected treprostinil (7) and FDKP (3) as shown in Scheme 2. The pure FDKP-treprostinil-side chain ester (9) was characterized by IR, $^1$H NMR, DQF-COSY and LCMS.

Experimental:

Synthesis of TBDMS FDKP-Treprostinil TMSE Cyclopentyl Ring Ester (4, R=TMSE):

To a solution of TBDMS-treprostinil TMSE ester (1, R=TMSE) (0.50 g) in N,N-dimethylacetamide (DMA) (14 mL) was added (E)-3,6-bis[4-(N-carbonyl-2-propenyl)amidobutyl]-2,5-diketopiperazine (FDKP) (3) (0.44 g) EDCI·HCl (0.24 g) and DMAP (0.30 g) at room temperature under argon. The suspension reaction mixture was stirred and heated to 100° C. The reaction mixture became clear and light brown and was continued heating at 100° C. overnight. The reaction mixture was stopped heating and then evaporated in vacuo to remove DMA and other organic volatiles. The crude product was triturated with toluene (75 mL) and decanted of the toluene soluble product(s) (repeated two more times). The toluene insoluble product was dried under vacuum to give light brown solid (0.61 g). The crude product was chromatographed on reverse pre-packed column using water and acetonitrile mixture to give TBDMS treprostinil TMSE cyclopentyl FDKP ester (4, R=TMSE) (0.015 g) confirmed by LCMS.

Synthesis of FDKP-Treprostinil Cyclopentyl Ring Ester (6):

To a solution of TBDMS FDKP-treprostinil TMSE cyclopentyl ring ester (4, R=TMSE) (0.013 g) in dimethyl sulfoxide (0.75 mL) was added a solution of tetrabutylammonium fluoride (TBAF) (1.0 M in THF (0.12 mL) at room temperature under argon. The reaction mixture was stirred at room temperature overnight. After 22 h, the reaction mixture was checked by LCMS and showed the desired molecular weight for FDKP-treprostinil cyclopentyl ring ester (6) along with FDKP cleaved product i.e, treprostinil.

Synthesis of TBDMS FDKP-Treprostinil Benzyl Cyclopentyl Ring Ester (5, R=Benzyl):

To a solution of mono-TBDMS-treprostinil benzyl ester (6, R=benzyl) (3.17 g) in N,N-dimethylformamide (DMF) (90 mL) was added (E)-3,6-bis[4-(N-carbonyl-2-propenyl)amidobutyl]-2,5-diketopiperazine (FDKP) (3) (2.89 g) EDCI·HCl (1.54 g) and DMAP (1.54 g) at room temperature under argon. The suspension reaction mixture was stirred and heated to 100° C. The reaction mixture became brown turbid and was continued heating at 100° C. overnight. After 16 h, the reaction mixture was checked by LCMS for the desired product. Under similar reaction conditions, the two more batches of coupling reactions of 0.61 g of TBDMS-treprostinil benzyl ester (2, R=benzyl) and 0.55 g of (E)-3,6-bis[4-(N-carbonyl-2-propenyl)amidobutyl]-2,5-diketopiperazine (FDKP) (3) were carried out and checked by LCMS. These three batches were combined based on LCMS data. The reaction mixture was evaporated in vacuo to remove DMF and other organic volatiles to give dark brown viscous liquid (18.37 g). The crude product was triturated with dichloromethane (3×100 mL) and filtered. The dichloromethane insoluble product (brown solid) was discarded and the dichloromethane soluble product was concentrated in vacuo to give brown viscous semi-solid product (14.59 g). The crude product was triturated with toluene (3×100 mL) and filtered. The toluene soluble product (7.02 g after evaporation of toluene) was discarded. The toluene insoluble product was dried under vacuum to give brown semi-solid (5.02 g). The crude product (5.0 g) was chromatographed on silica gel (188 g) column (230-400 mesh) using methanol in dichloromethane (0-100%) to give TBDMS FDKP-treprostinil benzyl cyclopentyl ring ester (5, R=benzyl) (2.26 g) confirmed by LCMS. The purified product contained some DMAP which could be eliminated in the next step. The 1.0 g of this purified product further purified by chromatographed on reverse pre-packed column using water and acetonitrile mixture containing 0.05% trifluoroacetic acid to give pure TBDMS FDKP-treprostinil benzyl cyclopentyl ring ester (5, R=benzyl) (0.085 g) confirmed by LCMS.

Synthesis of FDKP Treprostinil Cyclopentyl Ring Ester (14):

To a solution of crude mono-TBDMS FDKP treprostinil benzyl cyclopentyl ring ester (13, R=benzyl) (1.04 g) in 1,2-dichloroethane (25 mL) was added trimethyltin hydroxide (1.46 g) at room temperature under argon. The reaction mixture was heated at 60° C. overnight. After 19 h, the reaction was checked by LCMS and found complete. The reaction mixture was evaporated in vacuo to give light orange solid. (2.91 g). The crude product (1.45 g) was purified by chromatographed on reverse pre-packed column using water and acetonitrile mixture containing 0.05% trifluoroacetic acid to give pure fractions. These fractions were combined after checking the LCMS of the selected fractions. The combined fractions were stored in refrigerator overnight. After 18 h, the TBDMS group was completely cleaved and confirmed by LCMS. The remaining crude product (1.45 g) was also purified similarly. Then, the both purified products were combined and lyophilized to give off-white FDKP-treprostinil cyclopentyl ring ester (6) as a white solid (0.212 g) and characterized by IR, $^1$H NMR and LCMS.

Synthesis of Mono-TBDMS FDKP-Treprostinil Benzyl Side Chain Ester (8):

To a solution of TBDMS-treprostinil benzyl ester (7) (5.57 g) in N,N-dimethylformamide (DMF) (150 mL) was added (E)-3,6-bis[4-(N-carbonyl-2-propenyl)amidobutyl]-2,5-diketopiperazine (FDKP) (3) (5.08 g) EDCI·HCl (2.69 g) and DMAP (3.43 g) at room temperature under argon. The suspension reaction mixture was stirred and heated to 100° C. The reaction mixture became brown turbid and was continued heating at 100° C. overnight. After 16 h, the reaction mixture was checked by LCMS for the desired product. The reaction mixture was evaporated in vacuo to remove DMF and other organic volatiles to give brown viscous liquid (22.86 g). The crude product was triturated with dichloromethane (3×100 mL) and filtered. The dichloromethane insoluble product (brown solid) was discarded and the dichloromethane soluble product was concentrated in vacuo to give brown viscous liquid product (17.33 g). The crude product was triturated with toluene (200 mL) and filtered. The toluene soluble product (9.30 g of semi-solid product after evaporation of toluene) was discarded. The toluene insoluble product was dried under vacuum to give brown foamy solid (7.73 g). The LCMS of this crude product showed the desired TBDMS FDKPtreprostinil benzyl side chain ester (8) (7.73 g) as major product. The crude product was used in the next step without further purification.

Synthesis of FDKP-Treprostinil Side Chain Ester (9):

To a solution of crude mono-TBDMS FDKP treprostinil benzyl side chain ester (8) (2.45 g) in 1,2-dichloroethane (100 mL) was added trimethyltin hydroxide (3.44 g) at room temperature under argon. The reaction mixture was heated at 60° C. overnight. After 17 h, the reaction mixture was checked by LCMS and found complete. The reaction mixture was cooled to room temperature. The dichloroethane layer was decanted off from the brown viscous liquid (gummy). The dichloroethane layer was evaporated in vacuo to give light brown viscous liquid (4.48 g). The LCMS of this product showed very little product. The gummy brown product was dried under high vacuum to give a foamy brown solid (1.02 g) and contained a major desired product. The crude product (1.0 g) was purified by chromatographed on reverse phase pre-packed column using water and acetonitrile mixture containing 0.05% trifluoroacetic acid to give pure fractions. These fractions were combined after checking the LCMS of the selected fractions. The combined fractions were stored in refrigerator overnight. After 16 h, the TBDMS group was completely cleaved and confirmed by LCMS. The purified products were combined and lyophilized to give off white FDKP-treprostinil side chain ester (9) as an off-white solid (0.195 g) and characterized by IR, H NMR and LCMS and 98.85% purity by HPLC.

Example 2

This example relates to FDKP-treprostinil derivatives using DMSO as a polar solvent.

Synthesis of FDKP-Treprostinil TBDMS Cyclopentyl Ring Ester (5): Solvent: DMSO Scheme 3:

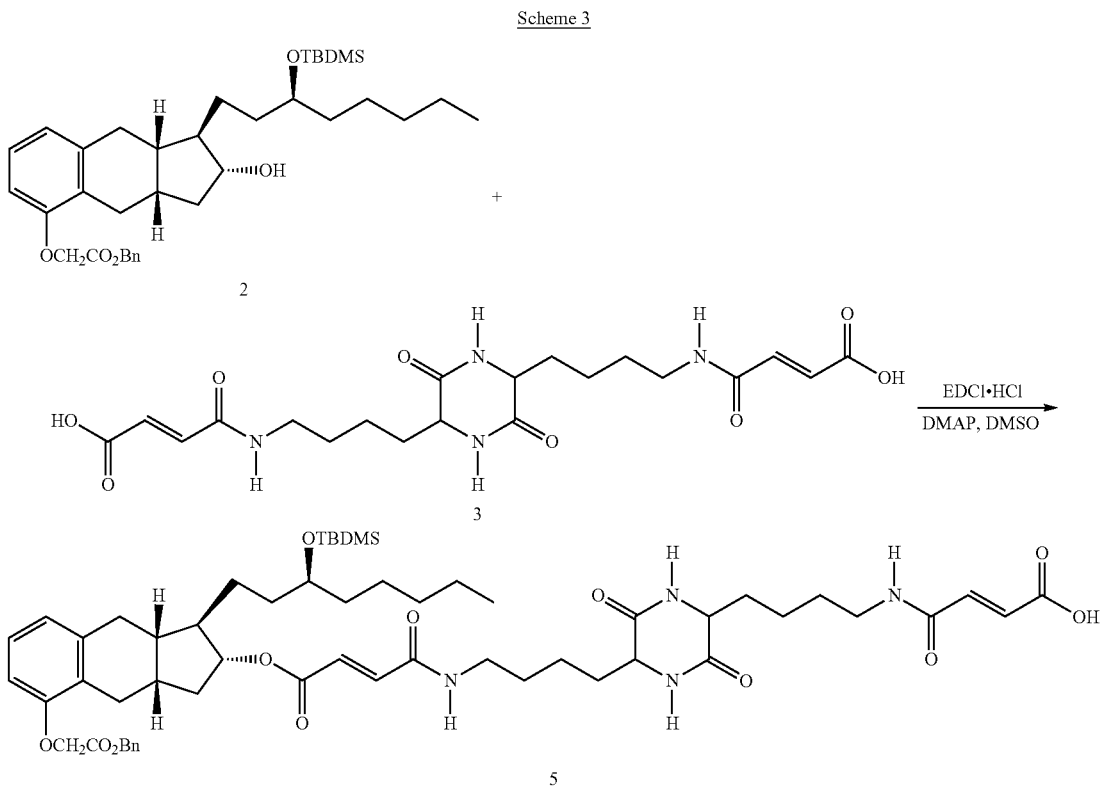

Experimental Procedure:

To a solution of mono-TBDMS treprostinil benzyl ester (2) (10.41 g, 17.50 mmol) in dimethylsulfoxide (DMSO) (100 mL) was added (E)-3,6-bis[4-(N-carbonyl-2-propenyl) amidobutyl]-2,5-diketopiperazine (FDKP) (3) (7.92 g, 17.50 mmol), EDCI·HCl (5.03 g, 26.34 mmol). To this white suspension DMAP (6.41 g, 52.47 mmol) was added the resulting light brown solution was stirred at room temperature under argon for 23 h. The reaction mixture was heated to 80° C. for two hours. The reaction mixture was cooled to room temperature and was diluted with dichloromethane (300 mL). This was passed through silica gel to remove DMSO using dichloromethane and then the compound was eluted with methanol. The fractions were combined and evaporated in vacuo to obtain brown liquid (5) (32.0 g).

Although Scheme 3 illustrates this synthesis using benzyl as a carboxylic acid protecting group and TBDMS as a hydroxyl protecting group other carboxylic acid protecting groups, including those from Example 1 and those discussed within this disclosure, and other hydroxyl protecting group, including those from Example 1 and those discussed within this disclosure, may be used instead of benzyl and TBDMS, respectfully. Double protected FDKP-treprostinil compound 5 may be deprotected as discussed elsewhere in this disclosure to obtained unprotected FDKP-Treprostinil Cyclopentyl Ring Ester.

Synthesis of FDKP-Treprostinil TBDMS Side Chain Ring Ester (8): Solvent: DMSO Scheme 4:

Scheme 4

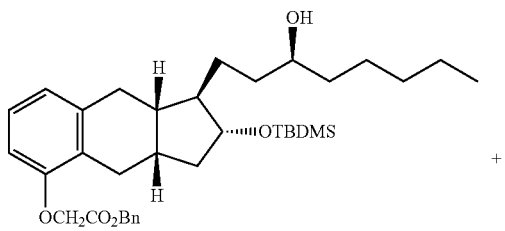

-continued

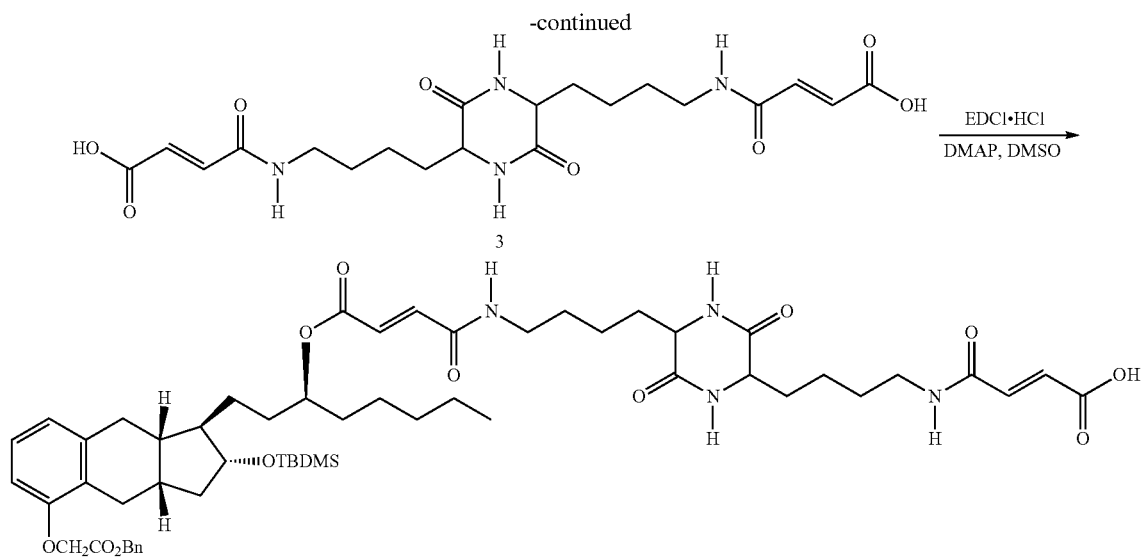

Experimental Procedure

To a solution of mono-TBDMS treprostinil benzyl ester (7) (12.60 g, 21.18 mmol) in dimethylsulfoxide (DMSO) (100 mL) was added (E)-3,6-bis[4-(N-carbonyl-2-propenyl)amidobutyl]-2,5-diketopiperazine (FDKP) (3) (9.58 g, 21.18 mmol), EDCI·HCl (6.098 g, 31.77 mmol). To this white suspension DMAP (7.76 g, 63.54 mmol) was added the resulting light brown solution was stirred at room temperature under argon for 23 h. The reaction mixture was heated to 80° C. for two hours. The reaction mixture was cooled to room temperature and was diluted with dichloromethane (300 mL). This was passed through silica gel to remove DMSO using dichloromethane and then the compound was eluted with methanol. The fractions were combined and evaporated in vacuo to obtain brown liquid (8) (34.7 g).

Although Scheme 4 illustrates this synthesis using benzyl as a carboxylic acid protecting group and TBDMS as a hydroxyl protecting group other carboxylic acid protecting groups, including those from Example 1 and those discussed within this disclosure, and other hydroxyl protecting group, including those from Example 1 and those discussed within this disclosure, may be used instead of benzyl and TBDMS, respectfully. Double protected FDKP-treprostinil compound 8 may be deprotected as discussed elsewhere in this disclosure to obtained unprotected FDKP-Treprostinil Side Chain Ester.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:
1. A compound of formula 5a or 5b:

or a pharmaceutically acceptable salt thereof,
wherein $R_5$ is H or a polymeric carrier.

2. The compound of claim 1, wherein the compound is the compound of formula 5a.

3. The compound of claim 1, wherein the compound is the compound of formula 5b.

4. The compound of claim 1, wherein $R_5$ is H.

5. The compound of claim 1, wherein $R_5$ is a polymeric carrier.

6. A pharmaceutically acceptable batch comprising the compound of claim 1 having a purity of at least 90%.

7. A pharmaceutical composition comprising the compound of claim 1 and a pharmaceutically acceptable excipient.

8. A method of making an FDKP-treprostinil compound comprising:

i) double-protecting treprostinil (1)

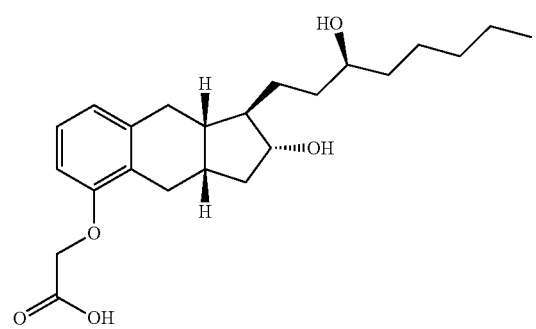 [SMILES: CCCCC[C@H](O)CC[C@@H]1[C@H]2Cc3cccc(OCC(=O)O)c3C[C@H]2C[C@H]1O]

to form a double-protected treprostinil moiety (2)

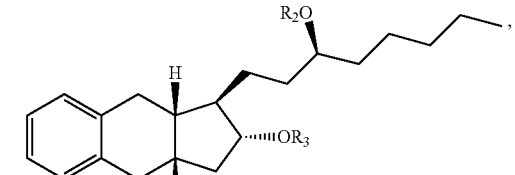

wherein $R_1$ is a carboxylic acid protecting group and wherein a) $R_2$ is H and $R_3$ is a hydroxyl protecting group or b) $R_2$ is a hydroxyl protecting group and $R_3$ is H;

ii) reacting the double-protected treprostinil moiety with a compound of formula (3)

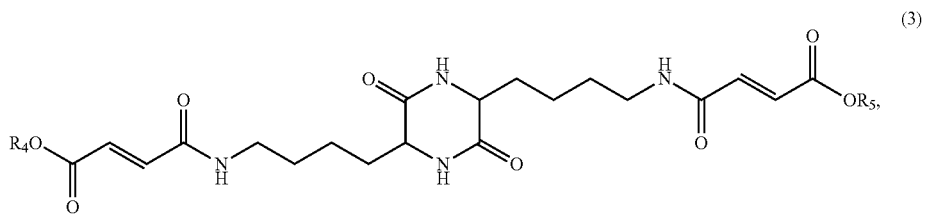

wherein $R_4$ is H, to form a double-protected FDKP-treprostinil compound having formula (4a) or (4b); and

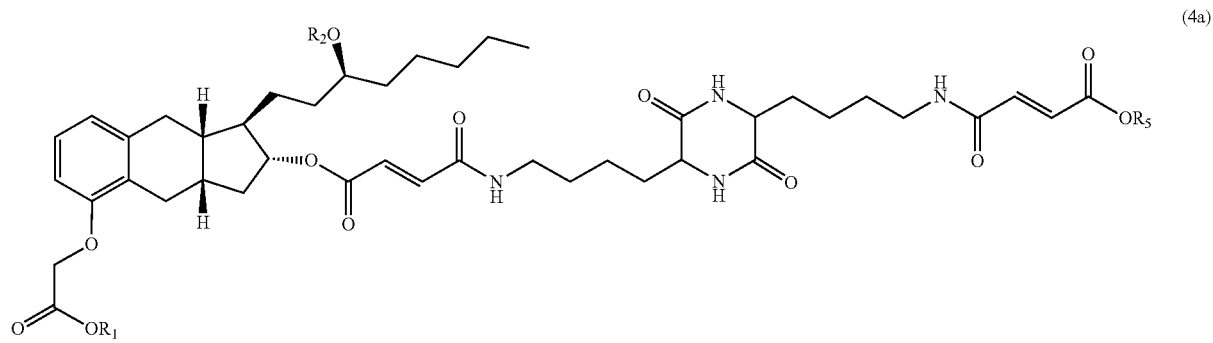

-continued

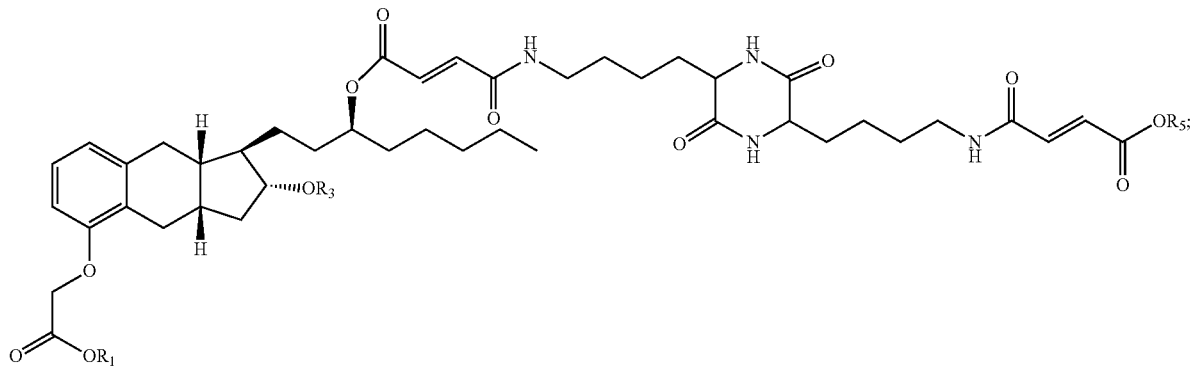

and
iii) deprotecting the double-protected FDKP-treprostinil compound to form an FDKP-treprostinil compound having formula (5a) or (5b)

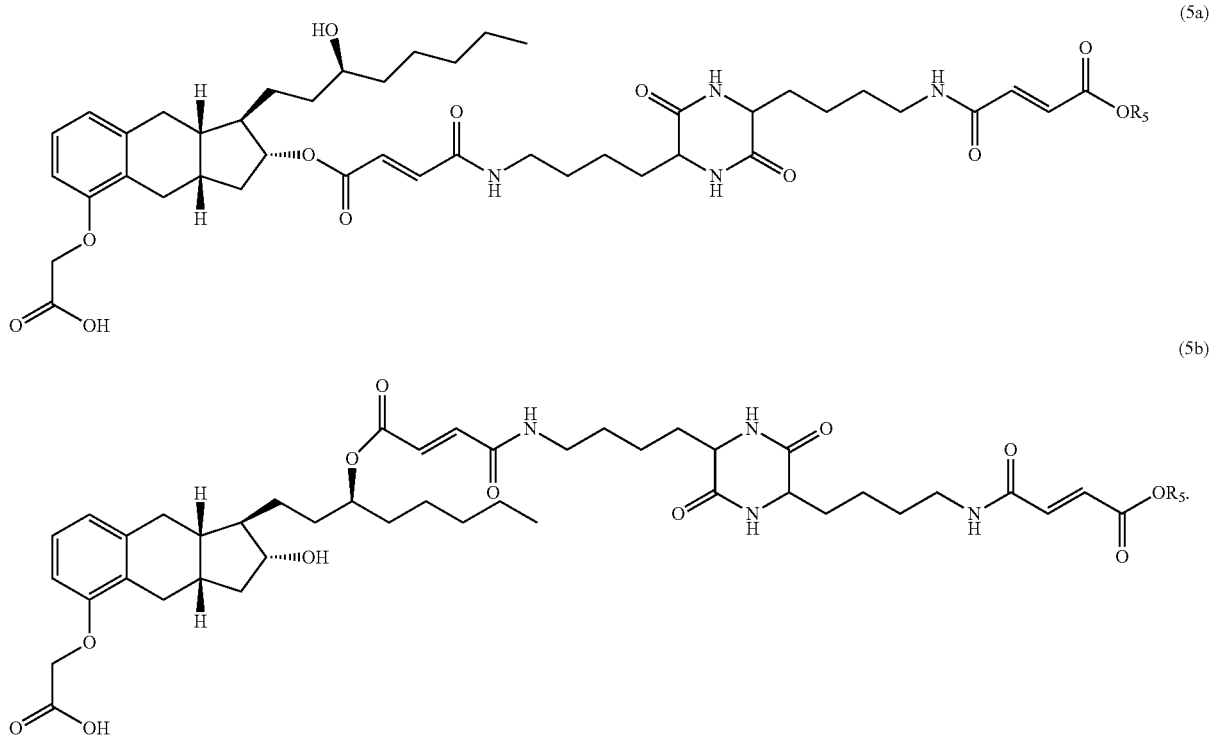

9. The method of claim 8, wherein $R_1$ is a silyl carboxylic acid protecting group or a substituted or unsubstituted benzyl carboxylic acid protecting group.

10. The method of claim 9, wherein $R_1$ is a silyl carboxylic acid protecting group selected from trimethylsilyl, triethylsilyl, tri-iso-propylsilyloxymethyl, triisopropyl silyl, t-butyldimethylsilyl, t-butyldiphenylsilyl, and phenyldimethylsilyl.

11. The method of claim 9, wherein $R_1$ is a substituted or unsubstituted benzyl carboxylic acid protecting group.

12. The method of claim 8, wherein the $R_2$ is H and $R_3$ is a hydroxyl protecting group, the double protected FDKP-treprostinil compound has formula (4b) and the FDKP-treprostinil compound has formula (5b).

13. The method of claim 8, wherein the $R_3$ is H and $R_2$ is a hydroxyl protecting group, the double protected FDKP-treprostinil compound has formula (4a) and the FDKP-treprostinil compound has formula (5a).

14. The method of claim 8, wherein said reacting the double protected treprostinil moiety with the compound of formula (3) was performed in the presence of a carbodiimide and a nucleophilic catalyst in a polar solvent.

15. The method of claim 14, wherein said reacting is performed in the presence of an organic base.

16. The method of claim 11, wherein the said deprotecting comprises deprotecting the double protected FDKP-treprostinil compound to form a single protected FDKP-treprostinil compound of formula (6a) or (6b):

(6a)

(6b)

17. The method of claim 16, wherein deprotecting the double protected FDKP-treprostinil compound to form the single protected FDKP-treprostinil compound is performed in the presence of a chemoselective benzyl cleavage agent.

18. The method of claim 8, wherein a purity of the FDKP-treprostinil compound is at least 90%.

19. A method of treating a treprostinil-treatable condition comprising administering to a subject in need thereof the compound of claim 1.

20. The method of claim 19, wherein the condition is pulmonary hypertension.

* * * * *

UNITED STATES PATENT AND TRADEMARK OFFICE
CERTIFICATE OF CORRECTION

| | | |
|---|---|---|
| PATENT NO. | : 11,793,780 B2 | Page 1 of 1 |
| APPLICATION NO. | : 17/342377 | |
| DATED | : October 24, 2023 | |
| INVENTOR(S) | : Hitesh Batra et al. | |

It is certified that error appears in the above-identified patent and that said Letters Patent is hereby corrected as shown below:

On the Title Page

Item [54] and in the Specification, Column 1, Line 1 In the TITLE: "TREPROSIINIL" should be --TREPROSTINIL--

Signed and Sealed this
Thirteenth Day of February, 2024

Katherine Kelly Vidal
*Director of the United States Patent and Trademark Office*